(12) United States Patent
Couturier et al.

(10) Patent No.: US 6,495,720 B1
(45) Date of Patent: Dec. 17, 2002

(54) METHOD FOR PREPARING ALKOXYAMINES FROM NITROXIDES

(75) Inventors: Jean-Luc Couturier, Lyons (FR); Olivier Guerret, Marcy l'Etoile (FR); Thierry Senninger, Hayange (FR)

(73) Assignee: Atofina, Paris la Defense (FR)

( * ) Notice: Subject to any disclaimer, the term of this patent is extended or adjusted under 35 U.S.C. 154(b) by 0 days.

(21) Appl. No.: 09/719,042

(22) PCT Filed: Mar. 24, 2000

(86) PCT No.: PCT/FR00/00750

§ 371 (c)(1),
(2), (4) Date: Feb. 23, 2001

(87) PCT Pub. No.: WO00/61544

PCT Pub. Date: Oct. 19, 2000

(30) Foreign Application Priority Data

Apr. 8, 1999 (FR) .............................. 99/04405

(51) Int. Cl.⁷ ............................. C07C 239/20
(52) U.S. Cl. ........................ 564/301; 546/184; 546/192; 558/87; 558/175; 564/300
(58) Field of Search ................. 564/300, 301; 558/87, 175; 546/184, 192

(56) References Cited

FOREIGN PATENT DOCUMENTS

| EP | 0 157 738 | 10/1985 |
|----|-----------|---------|
| WO | 9840415   | 9/1998  |

*Primary Examiner*—Richard L. Raymond
(74) *Attorney, Agent, or Firm*—Millen, White, Zelano & Branigan, P.C.

(57) ABSTRACT

The invention relates to a process for preparing alkoxyamines. This process consists in mixing, in an organic solvent, a metal salt, a ligand for the metal, a halocarbon compound ZX and a nitroxide, in keeping the reaction medium stirring at a temperature of between 20° C. and 90° C. until the nitroxide has disappeared, in recovering the organic phase, in washing it with water and then in isolating the alkoxyamine by evaporating the organic solvent under reduced pressure.

27 Claims, No Drawings

METHOD FOR PREPARING ALKOXYAMINES FROM NITROXIDES

This application is a 371 of pct/FR00/00750, filed Mar. 24, 2000.

The present invention relates to a process for preparing α,β,β-trisubstituted hydroxylamines, referred to hereinbelow as alkoxyamines, obtained from nitroxides, which can be used in particular as radical-polymerization initiators. The use of alkoxyamines such as those derived from (2,2,6,6-tetramethylpiperidyl)-N-oxide (TEMPO) in the preparation of macromolecules has given rise to many publications.

Thus, Hawker C. J. et al. (Macromolecules 1996, 29, pages 5245–5254) showed that the use of TEMPO-based alkoxyamines such as (2',2',6',6'-tetra-methyl-1'-piperidyloxy)methylbenzene as initiators for the radical-mediated polymerization of styrene made it possible to control the polymerization and to gain access to well-defined polymers with low polydispersity indices, and they found that the polymerization rates were substantially equivalent to the rates obtained when they used conventional initiators such as AIBN or benzoyl peroxide in the presence of TEMPO.

Alkoxyamines can be prepared according to methods known in the literature. The most common method involves the coupling of a carbon radical with a nitroxide radical.

If an alkoxyamine is denoted by:

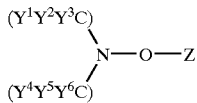
(I)

$Y^1$, $Y^2$, $Y^3$, $Y^4$, $Y^5$, $Y^6$, Z being defined later, the carbon radical Z* can be generated by various methods described in the literature: decomposition of an azo compound, abstraction of a hydrogen atom from a suitable substrate, addition of a radical to an olefin. The radical Z* can also be generated from an organometallic compound such as an organomagnesium reagent Z-MgX as described by Hawker C. J. et al. in Macromolecules 1996, 29, 5245–5254 or from a halo derivative Z-X in the presence of an organometallic system such as CuX/bipyridine (X=Cl or Br) according to a reaction of ATRA (Atom Transfer Radical Addition) type as described by Dorota Greszta et al. in Macromolecules 1996, 29, 7661–7670.

One of the methods most commonly used for preparing alkoxyamines (I) is the method involving the ATRA reaction.

This method consists in transferring an atom or a group of atoms onto another molecule in the presence of a CuX/bipyridine organometallic system, in solvent medium, according to the scheme:

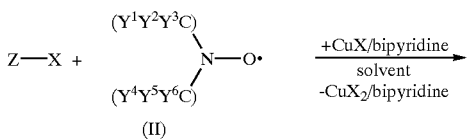

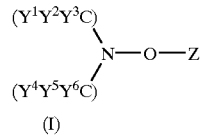
(I)

In the organometallic system, X preferably represents a bromine atom.

The procedure generally used consists in dissolving the organometallic system such as CuBr/bipyridine in an organic solvent, preferably an aromatic solvent such as benzene or toluene, and then in introducing the compound ZX and the nitroxide (II) into the solution.

This approach has the major drawback of requiring long reaction times, that are unacceptable for an industrial preparation of alkoxyamines, or of using a large excess of one of the reagents.

Furthermore, the organometallic system used involves expensive ligands (bipyridine or derivatives).

In addition, the removal of the residual metal from the products obtained is difficult, requiring expensive purification operations such as passing the products through a column of silica.

Thus, in international patent application WO 9B/40415, for example, Matyjaszewski K. et al. obtain 1-(2,2,6,6-tetramethylpiperidyloxy)-1-phenylethane in a yield of 69% after purification by column chromatography, by reactingTEMPO and (1-bromoethyl)benzene in a TEMPO/(1-bromoethyl)benzene molar ratio of 2 (i.e. a molar excess of TEMPO equal to 100%) for 2 hours at 90° C., in the presence of an organometallic system [4,4'-bis(5-nonyl)-2,2'-bipyridine/Cu(OTf)$_2$/Cu$^0$].

A process has now been found for preparing alkoxyamines of formula:

from nitroxides:

the said process consisting in reacting the said nitroxide (II) with a halocarbon compound ZX in which X represents a chlorine, bromine or iodine atom, in a water-immiscible organic solvent medium, in the presence of an organometallic system MA (L)n (III) in which:

M represents a metal such as Cu, Ag or Au,

A represents a halogen atom, a carboxylate group or a triflate group,

L represents a ligand for the metal M, n is 1, 2 or 3, according to the scheme:

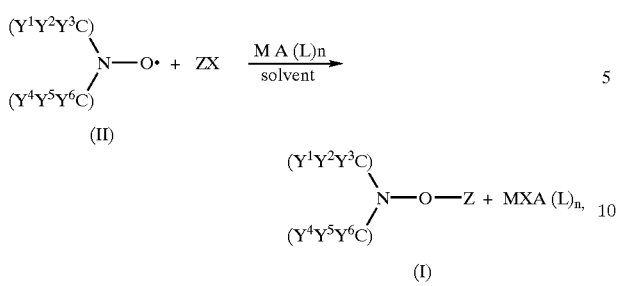

the said process being characterized in that it consists in carrying out the following steps:
a) a metal salt MA, the ligand L, the halocarbon compound ZX and the nitroxide (II) are mixed together with stirring, in an organic solvent, in a ZX/nitroxide (II) molar ratio ranging from 1 to 1.4,
b) the reaction medium is kept stirring at a temperature of between 20° C. and 90° C. until the nitroxide (II) has completely disappeared,
c) the organic phase is recovered and washed with water, and then
d) the alkoxyamine (I) is isolated by evaporating the organic solvent under reduced pressure.

Preferably, M represents Cu, A represents a halogen such as Cl or Br, a carboxylate group such as acetate or a triflate group, and X represents a chlorine atom or a bromine atom.

According to the present invention, the ligand L for the metal M in the organometallic system (III) is chosen from the compounds represented by the general formula (IV):

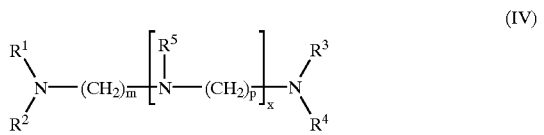

in which $R^1$, $R^2$, $R^3$ and $R^4$, which may be identical or different, represent a hydrogen atom, a linear or branched alkyl group containing a number of carbon atoms ranging from 1 to 10 and preferably ranging from 1 to 4, $R^5$ represents a hydrogen atom, a linear or branched alkyl group containing a number of carbon atoms ranging from 1 to 10 and preferably ranging from 1 to 4, a residue

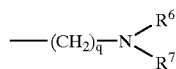

in which $R^6$ and $R^7$ have the same meanings as $R^5$, or alternatively at least two of the radicals $R^1$, $R^2$, $R^3$, $R^4$ and $R^5$ may be linked together to form a ring; m, p and q, which may be identical or different, represent integers ranging from 1 to 4, preferably equal to 2, x ranging from 0 to 4.

By way of illustration of ligands L represented by formula (IV) mention will be made of:
tris [2-(dimethylamino)ethyl]amine:

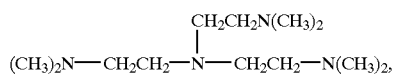

N,N,N',N',N''-pentamethyldiethylenetriamine (PMDETA):

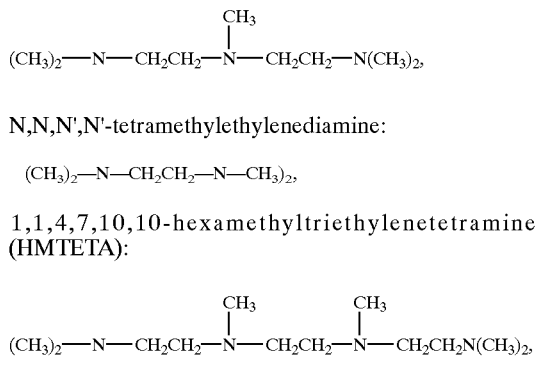

N,N,N',N'-tetramethylethylenediamine:

$(CH_3)_2—N—CH_2CH_2—N—(CH_3)_2,$ 1,1,4,7,10,10-hexamethyltriethylenetetramine (HMTETA):

cyclic polyamines such as:
1,4,7-trimethyl-1,4,7-triazacyclononane,
1,5,9-trimethyl-1,5,9-triazacyclododecane,
1,4,8,11-tetramethyl-1,4,8,11-tetraazacyclotetradecane.

PMDETA will preferably be used.

The process according to the invention consists in mixing, with stirring, a metal salt MA, the ligand L, the compound ZX and the nitroxide (II) in an organic solvent which is preferably an aromatic hydrocarbon such as benzene, toluene or xylenes, or an alkylchloride such as $CH_2Cl_2$ or alternatively an ether.

The oxidation state of the active species of the metal M is equal to 1 ($M^I$)

According to the present invention, this active species can be added, without modification, to the reaction medium, preferably in the form of a metal halide $M^I A$.

The preferred metal halide is CuBr.

The active species can also be generated in situ according to the redox reaction:

from a metal salt $M^{II}A$ in which the metal M is in oxidation state 2 ($M^{II}$) and the same metal in oxidation state zero ($M^O$).

According to this variant, the metal halide $M^{II}A$ which is preferred is $CuBr_2$.

According to another variant, a metal salt MA in which the metal M is in oxidation state 1 ($M^I A$) and the same metal M in oxidation-state zero ($M^O$) may also be introduced into the reaction medium.

The ligand L is used in an $L/M^I$ molar ratio ranging from 1 to 5 and preferably ranging from 1 to 2.

The ZX/nitroxide (II) molar ratio ranges from 1 to 1.4 and is preferably equal to 1.

The reaction mixture is then stirred at a temperature of between 20° C. and 90° C. and preferably in the region of room temperature.

The process is performed under an atmosphere of inert gas such as nitrogen or argon and preferably at atmospheric pressure.

The reaction times are very short. The end of the reaction can be monitored by the disappearance of the reagents, by chromatographic methods (GC, HPLC, TLC). Once the reaction is complete,. any precipitate obtained. is filtered off, rinsed, preferably with the same solvent used in the reaction, and the organic phase is then washed with water until the extracted aqueous phases become colorless.

The organic solvent is removed under reduced pressure, preferably at room temperature, and the alkoxyamine is recovered.

According to the invention, the water used to wash the organic phase can contain one or more salts in weight amounts that are not more than the solubility limit of the said salts in water at room temperature.

These salts will preferably be chosen from alkali metal salts, ammonium salts and alkylammonium salts of chloride, formate or oxalate.

By way of illustration of such salts which can be used according to the present invention, mention will be made of sodium chloride, ammonium. formate, triethylammonium formate and diammonium oxalate.

The alkoxyamines may be characterized by elemental analysis, HPLC, IR and NMR.

The process according to the invention has the advantage of being carried out with commercially available ligands. The reaction between the nitroxide (II) and the halocarbon compound ZX is fast. The removal of the metal M of the organometallic system MAa(L)n is particularly easy to carry out by simple washing with water.

The process according to the invention produces alkoxyamines that are virtually free of metal M.

In the alkoxyamines obtained according to the process of the invention, the content of metal M is less than 10 ppm.

In addition, the alkoxyamine yields are high.

The process according to the invention applies most particularly to the preparation of alkoxyamines of formula:

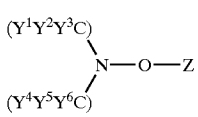
(I)

from nitroxides of formula:

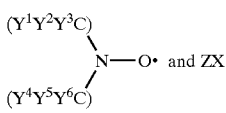
(II)

in which formulae the groups $Y^1$ to $Y^6$, which may be identical or different, represent a hydrogen atom, a linear or branched alkyl radical containing a number of carbon atoms ranging from 1 to 10, a cycloalkyl radical containing a number of carbon atoms ranging from 3 to 20, a halogen atom, a cyano radical, a phenyl radical, a hydroxyalkyl radical containing a number of carbon atoms ranging from 1 to 4, a dialkoxyphosphonyl or diphenoxyphosphonyl radical, an alkoxycarbonyl or alkoxycarbonylalkyl radical, or alternatively two or more of the groups $Y^1$ to $Y^6$ can be linked with the carbon atom which bears them to form cyclic structures, which can comprise one or more exocyclic functions chosen from: HO—, $CH_3C(O)$—, $CH_3O$—, $H_2N$—$CH_3C(O)NH$—, $(CH_3)_2N$—; or alternatively can comprise one or more exocyclic or endocyclic hetero atoms such as O or N;

Z is a residue of formula

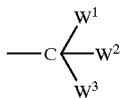

in which $W^1$, $W^2$ and $W^3$, which may be identical or different, represent a hydrogen atom, a linear or branched alkyl radical containing a number of carbon atoms ranging from 1 to 10, a phenyl radical, a benzyl radical, a cyano radical, a cycloalkyl radical containing a number of carbon atoms ranging from 3 to 12; a radical —$(CH_2)rC(O)OW^4$ in which $W^4$ represents a linear or branched alkyl containing a number of carbon atoms ranging from 1 to 6, r=0 to 6;

X represents a chlorine, bromine or iodine atom.

By way of illustration of nitroxides (II) which can be used according to the present invention, mention will be made of:

2,2,5,5-tetramethyl-1-pyrrolidinyloxy (generally sold under the trade name PROXYL);

3-carboxy-2,2,5,5-tetramethylpyrrolidinyloxy (commonly known as 3-carboxy PROXYL);

2,2,6,6-tetramethyl-1-piperidyloxy (commonly known as TEMPO);

4-hydroxy-2,2,6,6-tetramethyl-1-piperidyloxy (commonly known as 4-hydroxy-TEMPO);

4-methoxy-2,2,6,6-tetramethyl-1-piperidyloxy (commonly known as 4-methoxy-TEMPO);

4-oxo-2,2,6,6-tetramethyl-1-piperidyloxy (commonly known as 4-oxo-TEMPO);

4-amino-2,2,6,6-tetramethyl-1-piperidyloxy (commonly known as 4-amino-TEMPO);

4-acetamido-2,2,6,6-tetramethyl-1-piperidyloxy (commonly known as 4-acetamido-TEMPO);

N-tert-butyl-1-phenyl-2-methylpropyl nitroxide,

N-(2-hydroxymethylpropyl)-1-phenyl-2-methylpropyl nitroxide,

N-tert-butyl-1-diethylphosphono-2,2-dimethylpropyl nitroxide,

N-tert-butyl-1-dibenzylphosphono-2,2-dimethylpropyl nitroxide,

N-tert-butyl-1-di(2,2,2-trifluoroethyl)-phosphono-2,2-dimethylpropyl nitroxide,

N-tert-butyl-[(1-diethylphosphono)-2-methylpropyl] nitroxide,

N-(1-methylethyl)-1-cyclohexyl-1-(diethylphosphono) nitroxide,

N-(1-phenylbenzyl)-[(1-diethylphosphono)-1-methylethyl]nitroxide,

N-phenyl-1-diethylphosphono-2,2-dimethylpropyl nitroxide,

N-phenyl-1-diethylphosphono-1-methylethyl nitroxide,

N-(1-phenyl-2-methylpropyl)-1-diethylphosphonomethylethyl nitroxide, bis-1-oxyl-2,2,6,6-tetramethylpiperid-4-yl sebacate sold under the brand name "CXA 5415" by the company CIBA SPEC. CHEM.

By way of illustration of compounds ZX which can be used, mention will be made of the compounds of formula: $C_6H_5CH_2Br$, $(CH_3)_2C(CN)$ Br, $CH_3OC(O)C(CH_3)_2Br$, $CH_3OC(O)CH(CH_3)Br$, $C_6F_{13}I$.

The alkoxyamines of formula (I) obtained according to the process of the present invention can be used for the polymerization and copolymerization of any monomer containing a carbon-carbon double bond which can undergo radical-mediated polymerization. The polymerization or copolymerization is carried out under the usual conditions known to those skilled in the art, taking into account the monomer(s) under consideration. The monomers under consideration may be a vinylaromatic monomer (styrene, substituted styrenes), a diene or an acrylic or methyacrylic monomer. The monomer may also be vinyl chloride, vinylidene difluoride or acrylonitrile.

The examples which follow illustrate the invention.

EXAMPLES

GENERAL COMMENTS

The tests were carried out under an atmosphere of inert gas (argon or nitrogen) using Schlenk techniques (standard).

The 1-bromoethylbenzene and N-tert-butyl-1-diethylphosphono-2,2-dimethylpropyl nitroxide (DEPN) are degassed beforehand.

The solvents used are toluene, which is distilled beforehand under argon over sodium-benzophenone, and $CH_2Cl_2$.

The ligands used are:
N,N,N',N',N''-pentamethyldiethylenetriamine, denoted hereinbelow as PMDETA,
tris(2-pyridylmethyl)amine, denoted hereinbelow as TPA,
bipyridine, denoted hereinbelow as BIPY.

The alkoxyamines obtained were characterized by $^1H$, $^{13}C$ and $^{31}P$ NMR and by elemental analysis.

The residual copper contents were determined by the plasma atomic emission spectroscopy technique with detection by mass spectrometry, referred to hereinbelow as ICP-MS (Inductively Coupled Plasma—Mass Spectrometry).

Example 1

Not in Accordance with the Invention

Preparation of N-tert-Butyl-N-1-diethylphosphono-2,2-dimethylpropyl-O-1-phenylethylhydroxylamine

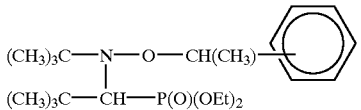

0.57 g of CuBr (4 mmol) and 1.25 g of BIPY (8 mmol) (BIPY/CuBr molar ratio=2) are introduced into a 100 ml Schlenk tube purged with argon. 0.74 g of (1-bromoethyl) benzene (4 mmol) and 0.68 g of 86% DEPN (2 mmol) dissolved in 9 ml of anhydrous toluene are added. The mixture is left to react for 48 hours at room temperature, with stirring. The reaction mixture is filtered through Celite. The filtrate is washed with aqueous 5% copper sulphate solution and then with water. The organic phase is dried over magnesium sulphate and the solvent is then evaporated off. A greenish oil containing copper is obtained, which is purified by chromatography on a column of silica using a 6/4 pentane/ether eluent. 0.75 g of N-tert-butyl-N-1-diethylphosphono-2,2-dimethylpropyl-O-1-phenylethylhydroxylamine is obtained (yield=95%) in the form of two diastereoisomers in 64/36 proportions determined from the $^{31}P$ spectrum of the crude mixture by integration of the signals at 23.14 and 24.36 ppm (I/II=64/36).

The analytical results are given below:

Isomer I:
$^{31}P$ NMR (CDCl$_3$): δ 23.14; $^1H$ NMR (CDCl$_3$): δ 0.88 (t, $J_{H-H}$=7.2 Hz, 3H): 1.27 (m, 21H); 1.55 (d, $J_{HH}$=6.6 Hz, 3H) (s, 9H); 3.40 (d, $J_{H-P}$=26 Hz, 1H); 3.18–3.40 and 3.70–4.05 (m, 4H); 5.22 (q, $J_{H-H}$=6.6 Hz, 1H); 7.24–7.47 (m, 5H).
$^{13}C$ NMR (CDCl$_3$): δ 16.23 (2d, $J_{C-P}$=7 Hz, $\underline{C}H_3CH_2$), 21.18 (s, $\underline{C}H_3CH$), 28.19 (s, $CH_3$—C—CH), 30.63 (d, $J_{C-P}$=7 Hz, $\underline{C}H_3$—CN), 35.33 (d, $j_{C-}$=6 Hz, $\underline{C}$—CH—P), 58.58 (d, $J_{C-P}$=7.5 Hz, $\underline{C}$—CH$_3$), 61.4 (d, $j_{C-P}$=7 Hz, $\underline{C}H_2$—O), 70.06 (d, $j_{C-P}$=138.5 Hz, $\underline{C}H$-P), 78.36 (s, $\underline{C}H$—O), 127.33 (s, $\underline{C}H$ Ar), 127.81 (s, $\underline{C}H$ Ar), 127.88 (s, $\underline{C}H$ Ar), 143.31 (s, $\underline{C}H$ Ar).

Microanalysis ($C_{21}H_{37}NO_4P$): % calculated C, 63.12; H, 9.59; N, 3.51. % found C, 63.01; H, 9.60; N, 3.42.

Isomer II:
$^{31}P$ NMR (CDCl$_3$): δ 24.36; $^1H$ NMR (CDCl$_3$): δ 0.82; (s, 9H); 1.22 (s, 9H), 1.29 (t, $J_{H-H}$=7.0 Hz, 3H); 1.32 (t, $J_{H-H}$=7.0 Hz, 3H); 1.58 (d, $J_{H-H}$=6.7 Hz, 3H); 3.32 (d, $J_{H-P}$=26.2 Hz, 1H); 3.9–4.2 and 4.3–4.4 (m, 4H); 4.97 (q, $J_{H-H}$=6.8 Hz, 1H); 7.17–7.3 (m, 5H).
$^{13}C$ NMR (CDCl$_3$): δ 16.24 (d, $J_{C-P}$=7.1 Hz, $\underline{C}H_3CH_2$), 16.71 (d, $J_{C-P}$=5.2 Hz, $\underline{C}H_3CH_2$), 24.00 (s, $\underline{C}H_3CH$), 28.50 (s, $\underline{C}H_3$—C—CH), 30.12 (d, $J_{C-P}$=5.7 Hz, $\underline{C}H_3$—C—N), 35.37 (d, $j_{C-P}$=5.8 Hz, $\underline{C}$—$C_{H-P}$), 58.80 (d, $J_{C-P}$=7.4 Hz, $\underline{C}H_2$—O), 61.10 (s, C—N), 61.56 (d, $J_{C-P}$=6 Hz, $\underline{C}H_2$—O), 69.84 (d, $J_{C-P}$=138.4 Hz, $\underline{C}H$—P), 85.23 (s, $\underline{C}H$—O), 126.96 (s, $\underline{C}H$ Ar), 127.08 (s, $\underline{C}H$ Ar), 127.95 (s, $\underline{C}H$ Ar), 145.36 (s, $\underline{C}$ Ar).

Microanalysis ($C_{21}H_{37}NO_4P$): % calculated C, 63.12; H, 9.59; N, 3.51. % found C, 63.05; H, 9.51; N, 3.50.

Example 2

In Accordance with the Invention

Preparation of N-tert-Butyl-N-1-Diethylphosphono-2,2-dimethylpropyl-O-1-phenylethylhydroxylamine Use of PMDETA instead of BIPY:

0.46 g of CuBr (3.21 mmol) and 1.11 g of PMDETA (6.42 mmol) are introduced into a 100 ml Schlenk tube. The tube is purged with vacuum-argon sequences, after which 0.59 g of (1-bromoethyl)benzene (3.21 mmol) and 1 g of 70% DEPN (2.38 mmol) diluted in 10 ml of toluene are added. The mixture is left to react for 30 minutes at room temperature, with stirring. The reaction mixture is filtered through Celite and the filtrate is then washed with water (5 times 30 ml of water). The solvent is evaporated off to give 0.98 g of N-tert-butyl-N-1-diethylphosphono-2,2-dimethylpropyl-O-1-phenylethylhydroxylamine in the form of a colorless oil.

The purity of the product, analysed by HPLC, is 97%. The yield is close to 100%. The analytical characteristics are identical to the alkoxyamine obtained in Example 1.

The residual Cu content is less than 10 ppm.

Example 3

In Accordance with the Invention

Preparation of 1-(2,2,6,6-Tetramethylpiperidyloxy)-1-phenylethane

The reaction takes place under a nitrogen atmosphere.

10 ml of toluene, 0.4 g of copper, 0.84 g of CuBr and 1 g of PMDETA are introduced into a 100 ml Schlenk tube.

The solution is degassed under reduced pressure and 10 ml of degassed toluene containing 0.92 g of TEMPO (0.0059 mol) and 1.1 g of (1-bromoethyl)benzene (0.0059 mol) are then added thereto.

The addition is exothermic. After 30 minutes, the disappearance of the reagents is checked by thin layer chromatography (TLC). The organic solution is filtered and is then washed with water until the aqueous phases are colorless. The toluene is then evaporated off to give 1.5 g of 1-(2,2, 6,6-tetramethylpiperidyloxy)-1-phenylethane (97% yield), whose purity is checked by $^1$H and $^{13}$C NMR by comparison with the literature data.

The copper assay by ICP-MS shows that the copper content is less than 10 ppm.

Examples 4(NIA), 5(NIA) and 6

In Accordance with the Invention

N-tert-Butyl-N-1-diethylphosphono-2,2-dimethylpropyl-O-1-phenylethylhydroxylamine was prepared according to a procedure similar to that of Example 2, with various ligands L and according to procedures given in Table 1. The results obtained are given in Table 1. Examples 4 (NIA) and 5 (NIA) are not in accordance with the invention.

Example 7

In Accordance with the Invention

The reaction between DEPN and (1-bromo-ethyl)benzene is repeated under the same conditions as those described in Example 2, except that toluene is replaced with CH$_2$Cl$_2$. The TLC analysis after reaction for 5 minutes shows that all the reagents have reacted.

After washing with water, N-tert-butyl-N-1-diethylphosphono-2, 2-dimethylpropyl-O-1-phenylethyl-hydroxylamine isobtained in a yield of 91%. The copper content is less than 10 ppm. The results of this example are also given in Table 1.

TABLE 1

| Example | L | Solvent | L/Cu$^I$ | ZX/DEPN | Time (min) | Yield | Cu (ppm) |
|---|---|---|---|---|---|---|---|
| 4 (NIA) | BIPY | toluene | 2 | 2 | 240 | 2 | — |
| 5 (NIA) | TPA | toluene | 2 | 1.35 | 240 | 85 | 100 |
| 6 | PMDETA | toluene | 2 | 1 | 60 | 95 | <10 |
| 7 | PMDETA | CH$_2$Cl$_2$ | 1 | 1 | 5 | 91 | <10 |

Example 8

In Accordance with the Invention

Preparation of N-tert-Butyl-N-1-diethylphosphono-2,2-dimethylpropyl-O-1-phenylethylhydroxylamine In this example, the treatment is carried out with a triethylammonium formate solution. The triethylamronium formate is prepared by mixing formic acid and triethylamine in molar proportions of 1.5/1.

4.3 g of (1-bromoethyl)benzene (0.023 mol), 5.4 g of 93% DEPN (0.017 mol), 3.3 g of CuBr (0.023 mol), 4.0 g of PMDETA (0.023 mol), 1.45 g of copper powder (0.023 mol) and 50 g of degassed toluene are introduced into a 250 ml reactor purged with argon. The mixture is left to react for 3 h at 35° C., with stirring. The reaction mixture is filtered through Celite. The filtrate is washed with 25 g of an aqueous solution containing 40% by weight of triethylammonium formate, and then with water (2×25 g). The organic phase is evaporated under vacuum to give 6.1 g of N-tert-butyl—N—1-diethylphosphono-2,2-dimethylpropyl-O-1-phenylethylhydroxylamine in the form of a colorless oil (yield=90%; purity=97%). The residual Cu content is less than 10 ppm.

Example 9

Preparation of N-tert-butyl-N-1-diethylphosphono-2,2-dimethylpropyl-O -1-methoxycarbonylethylhydroxylamine 115 g of methyl 2-bromopropionate (0.687 mol), 200 g of 91% DEPN (0.619 mol), 49.3 g of CuBr (0.344 mol), 59.8 g of PMDETA (0.344 mol), 43.6 g of copper powder (0.687 mol) and 800 ml of degassed toluene are introduced into a 2 l reactor purged with argon. The mixture is left to react for 4 h at room temperature, with stirring. The reaction mixture is filtered through Celite. The filtrate is washed with an aqueous solution containing 40% by weight of ammonium formate (2×500 ml) and then with aqueous $_5$% potassium hydrogen carbonate solution (1×500 ml). The organic phase is evaporated under vacuum to give 212 g of N-tert-butyl—N—1-diethylphosphono-2,2-dimethylpropyl-O-1-methoxycarbonylethylhydroxylamine in the form of a slightly yellow oil (yield=90%, purity=98%). The residual Cu content is less than 10 ppm.

What is claimed is:

1. A process for preparing alkoxyamines of formula:

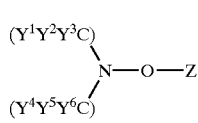

(I)

from nitroxides of formula:

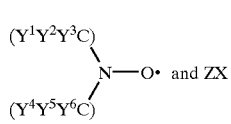

(II)

in which formulae the groups Y$^1$ to y$^6$, which may be identical or different, represent a hydrogen atom, a linear or branched alkyl radical containing a number of carbon atoms ranging from 1 to 10, a cycloalkyl radical containing a number of carbon atoms ranging from 3 to 20, a halogen atom, a cyano radical, a phenyl radical, a hydroxyalkyl radical containing a number of carbon atoms ranging from 1 to 4, a dialkoxyphosphonyl or diphenoxyphosphonyl radical, an alkoxycarbonyl or alkoxycarbonylalkyl radical, or alternatively two or more of the groups y$^1$ to Y6 can be linked with the carbon atom which bears them to form cyclic structures, which can comprise one or more exocyclic functions chosen from: HO—, CH$_3$C(O)—, CH$_3$O—, H$_2$N— CH$_3$C(O)NH—, (CH$_3$)$_2$N—; or alternatively can comprise one or more exocyclic or endocyclic hetero atoms selected from O and N;

Z is a residue of formula

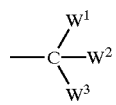

in which W$^1$, W$^2$ and W$^3$, which may be identical or different, represent a hydrogen atom, a linear or branched alkyl radical containing a number of carbon atoms ranging from 1 to 10, a phenyl radical, a benzyl radical, a cyano radical, a cycloalkyl radical containing a number of carbon atoms ranging from 3 to 12; a radical —CH$_2$)$_r$C(O)OW$^4$ in which W$^4$ represents a linear or branched alkyl containing a number of carbon atoms ranging from 1 to 6, and r=0 to 6;

X represents a chlorine, bromine or iodine atom, said process comprising reacting said nitroxide (II) with a halocarbon compound ZX, in a water-immiscible organic solvent medium , in the presence of an organometallic system MA(L)n (III) in which:

M represents a metal,
A represents a halogen atom, a carboxylate group or a triflate group,
L represents a ligand for the metal M,
n is 1, 2 or 3, according to the scheme:

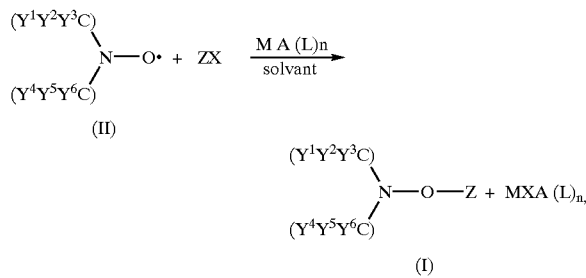

said process comprising carrying out the following steps:
a) a met al salt NU, the ligand L, the halocarbon compound ZX and the nitroxide (II) are mixed together with stirring, in an organic solvent, in a ZX/nitroxide (II) molar ratio ranging from 1 to 1.4,
b) the reaction medium is kept stirring at a temperature of between 20° C. and 90° C. until the nitroxide (II) has completely disappeared,
c) the organic phase is recovered and washed with water, and then
d) the alkoxyamine (I) is isolated by evaporating the organic solvent under reduced pressure and
in that the ligand L for the metal M in the organometallic system (III) is chosen from the compounds represented by the general formula (IV):

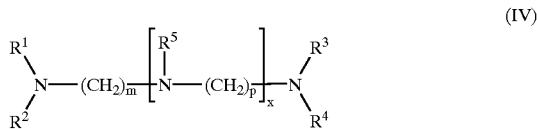

in which $R^1$, $R^2$, $R^3$ and $R^4$, which may be identical or different, represent a hydrogen atom, a linear or branched alkyl group containing a number of carbon atoms ranging from 1 to 10, $R^5$ represents a hydrogen at atom, a linear or branched alkyl group containing a number of carbon atoms ranging from 1 to 10, a residue

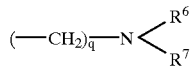

in which $R^6$ and $R^7$ have the same meanings as $R^5$, or alternatively at least two of the radicals $R^1$, $R^2$, $R^3$, $R^4$ and $R^5$ may be linked together to form a ring; m, p and q, which may be identical or different, represent integers ranging from 1 to 4, and x ranges from 0 to 4.

2. A process according to claim 1, wherein M is Cu, Ag or Au.

3. A process according to claim 2, characterized in that M represents Cu.

4. A process according to claim 2, characterized in that A represents a bromine atom and X represents a chlorine atom or a bromine atom.

5. A process according to claim 2, characterized in that the ZX/nitroxide (II) molar ratio is equal to 1.

6. A process according to claim 2, wherein the metal salt MA is a metal halide in which M has an oxidation state of 1.

7. A process according to claim 6, wherein the metal halide is CuBr.

8. A process according to claim 7, wherein the molar ratio L/M ranges from 1 to 5.

9. A process according to claim 8, wherein the molar ratio L/M ranges from 1 to 2.

10. A process according to claim 2, characterized in that the organic solvent is an aromatic hydrocarbon or an alkyl chloride.

11. A process according to claim 10, characterized in that the aromatic hydrocarbon is toluene and the alkyl chloride is methylene chloride.

12. A process according to claim 2, characterized in that the ligand L is:

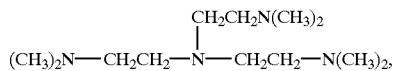

N,N,N',N',N"-pentamethyldiethylenetriamine (PMDETA):

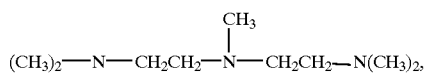

N,N,N',N'-tetramethylethylenediamine:

1,1,4,7,10,10-hexamethyltriethylenetetramine (HMTETA):

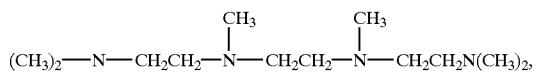

1,4,7-trimethyl-1,4,7-triazacyclononane,
1,5,9-trimethyl-1,5,9-triazacyclododecane, or
1,4,8,11-tetramethyl-1,4,8,11-tetraazacyclotetradecane.

13. A process according to claim 12, characterized in that the ligand L is N, N, N',N',N"-pentamethyldiethylenetriamine (PMDETA).

14. A process according to claim 2, characterized in that the water used to wash the organic phase contains one or more salts chosen from alkali metal salts, ammonium salts and alkylammonium salts of chloride, formate and oxalate salts.

15. A process according to claim 14, characterized in that the salt is triethylammonium formate.

16. A process according to claim 14, characterized in that the salt is ammonium formate.

17. A process according to claim 2, wherein at least one $R^1$, $R^2$, $R^3$, $R^4$ represents alkyl of 1–4 carbon atoms.

18. A process according to claim 2, wherein $R^5$ represents alkyl of 1–4 carbon atoms.

19. A process according to claim 2, wherein m, p and q are each equal to 2.

20. A process according to claim 2, wherein A represents a bromine atom and X represents a chlorine atom or a bromine atom.

21. A process according to claim 2, wherein the ZX nitroxide (II) molar ratio is equal to 1.

22. A process according to claim 3, wherein the ZX nitroxide (II) molar ratio is equal to 1.

23. A process according to claim 2, wherein the metal salt MA is a metal halide in which M has an oxidation state of 1.

24. A process according to claim 3, wherein the metal salt MA is a metal halide in which M has an oxidation state of 1.

25. A process according to claim 2, wherein the molar ratio L/M ranges from 1 to 5.

26. A process according to claim 3, wherein the molar ratio L/M ranges from 1 to 5.

27. A process according to claim 20, wherein the metal salt is CuBr and the molar ratio L/M ranges from 1 to 2.

* * * * *

UNITED STATES PATENT AND TRADEMARK OFFICE
CERTIFICATE OF CORRECTION

PATENT NO. : 6,495,720 B1  
DATED : December 17, 2002  
INVENTOR(S) : Jean-Luc Couturier et al.

It is certified that error appears in the above-identified patent and that said Letters Patent is hereby corrected as shown below:

Column 11,  
Line 21, reads "a met al salt NU" should read -- a metal salt MA --

Column 12,  
Lines 63 and 66, reads "claim 2," should read -- claim 3, --

Column 13,  
Lines 1 and 6, reads "claim 3," should read -- claim 4, --  
Line 3, reads "claim 2," should read -- claim 3, --

Column 14,  
Line 1, reads "claim 2," should read -- claim 3, --  
Line 3, reads "claim 3," should read -- claim 4, --

Signed and Sealed this

Seventeenth Day of February, 2004

JON W. DUDAS  
*Acting Director of the United States Patent and Trademark Office*

UNITED STATES PATENT AND TRADEMARK OFFICE
CERTIFICATE OF CORRECTION

PATENT NO. : 6,495,720 B1　　　　　　　　　　　　　　　　　　　　　　Page 1 of 1
DATED : December 17, 2002
INVENTOR(S) : Jean-Luc Couturier et al.

It is certified that error appears in the above-identified patent and that said Letters Patent is hereby corrected as shown below:

Column 10,
Line 30, reads "Y1 to y6," should read -- Y1 to Y6, --
Line 39, reads "y1 to Y6" should read -- Y1 to Y6 --
Line 60, reads "-CH2)rC(O)OW4" should read -- (CH2)rC(O)OW4 --

Column 11,
Line 46, reads "hydrogen at atom" should read -- hydrogen atom --

Signed and Sealed this

Eighteenth Day of May, 2004

JON W. DUDAS
*Acting Director of the United States Patent and Trademark Office*